United States Patent [19]

Briller et al.

[11] Patent Number: 4,751,931
[45] Date of Patent: Jun. 21, 1988

[54] METHOD AND APPARATUS FOR DETERMINING HIS-PURKINJE ACTIVITY

[75] Inventors: Stanley A. Briller, Sewickley; Gerald G. Cano, Pittsburgh, both of Pa.

[73] Assignee: Allegheny-Singer Research Institute, Pittsburgh, Pa.

[21] Appl. No.: 909,677

[22] Filed: Sep. 22, 1986

[51] Int. Cl.[4] .................... A61B 5/04; G06F 15/42
[52] U.S. Cl. .................................. 128/700; 128/696; 364/417
[58] Field of Search .............. 128/695, 696, 702, 708, 128/700; 364/417

[56] References Cited

PUBLICATIONS

IEEE Transactions on Circuits and Systems, vol. CAS-28, No. 6, Jun. 1981, p. 519-523, Ferrara & Widrow. Fetal Electrocardiogram Enhancement by Time-Sequenced Adaptive Filtering by E. Ferrara and B. Widrow IEEE Trans. on Biomedical Eng. Jun. 1982.
B. J. Scherlag et al., "Catheter Technique for Recording His Bundle Activity in Man," Circulation, 39:13, 1969.
E. J. Berbari et al., "Noninvasive Technique for Detection of Electrical Activity During the P-R Segment," Circulation, 48:1005, 1973.
N. C. Flowers et al., "Surface Recording of Electrical Activity from the Region of the Bundle of His," American Journal of Cardiology, 33:384, 1974.
Y. Hishimoto and T. Sawayama, "Non-Invasive Recording of His Bundle Potential in Man," British Heart Journal, 37:635, 1975.
R. Vincent et al., "Noninvasive Recording of Electrical Activity in the PR Segment in Man," British Heart Journal, 40:124, 1978.
H. Takeda et al., "Noninvasive Recording of His-Purkinje Activity in Patients with Complete Atrioventricular Block," Circulation, 60:421, 1979.
N. El-Sherif et al., "Appraisal of a Low Noise Electrocardiogram," Journal of the American College of Cardiology, 1(2):456, 1983.
N. C. Flowers et al., "Surface Recording of His-Purkinje Activity on an Every-Beat Basis without Digital Averaging," Circulation, 63:498, 1981.
S. N. Erne et al., "Beat to Beat Surface Recording and Averaging of His-Purkinje Activity in Man," Journal of Electrocardiology, 16(4):355, 1983.
E. R. Ferrara, Jr., "The Time-Sequenced Adaptive Filter," Stanford University, Ph.D. Thesis (1978).
B. Widrow et al., "Stationary and Nonstationary Learning Characteristics of the LMS Adaptive Filter," Proceedings of the IEEE, 64:1151, 1976.
M. T. Juran, "Surface Recordings of His-Purkinje Activity Using Adaptive Filtering," Carnegie-Mellon University, Masters Thesis (1984).

Primary Examiner—William E. Kamm
Assistant Examiner—George Manuel
Attorney, Agent, or Firm—Webb, Burden, Ziesenheim & Webb

[57] ABSTRACT

An apparatus and method for detecting low level bioelectric signals on the surface of a patient. The bioelectric signals are enhanced by filtering out noise through a particular adaptive filtering technique. In detecting His signals at the chest of a patient, surface ECG's are acquired at a plurality of external locations, the acquired data is digitized and stored. One of the ECG signals is selected as a reference channel and the remaining ECG signals are used as input channels. With the use of a feedback coefficient, each data point of interest in each cycle is adaptively filtered to remove the noise and the filtered signal is displayed. The adaptive filtering involves performing two pre-updates of a weight matrix associated with each sample point of each input channel based on the measured samples before and after a sample point, calculating an output signal based on the weight matrix and the input channel, and updating the weight matrices based on the calculated output signal.

29 Claims, 9 Drawing Sheets

METHOD AND APPARATUS FOR DETERMINING HIS-PURKINJE ACTIVITY

FIELD OF THE INVENTION

This invention relates to the surface detection of low level bioelectric signals and, more particularly, to the detection of His signals.

BACKGROUND ART

The bundle of His is a small mass of electrically excitable tissue originating in the atrial septum of the heart, the wall that separates the right and left sides of the heart. The His bundle divides into the right and left bundles which connect to the Purkinje system at the apex of the heart. The Purkinje system includes electrically excitable fibers which line both ventricles. The rhythm of the normal heart originates in the thin-walled right atrium and is transmitted via the His bundle and Purkinje system, a high speed electrical conduction system, to the thick-walled ventricles which perform the pumping function of the heart.

Recordings of His bundle electrical activity have been routinely used by physicians as a diagnostic tool to, for example, localize the site of atrioventricular conduction blocks, as well as to characterize the effects of drugs on conducting tissue within the heart. However, standard surface ECG records are ineffective for detecting His signals for several reasons. Conduction through the His-Purkinje cells is much faster than through the atria or ventricular muscles. Consequently, the His signal includes significant high frequency components, typically from 100-500 Hz. Standard ECG recorders are not designed to record such high frequency signals. In addition, the bundle of His is a small mass of tissue and voltages and currents associated with His activity and are of very low magnitude. The His signal has a normal amplitude of from 0.1 to 10 microvolts on the body surface. Competing myoelectric noise, created from muscle activity in the chest and the like, is usually of equal or greater magnitude than the His signal. The surface His signal is normally indistinguishable from this background noise. Furthermore, the myoelectric noise has a frequency spectrum similar to or overlapping that of the His signal. Therefore, neither amplification nor frequency filtering of a standard surface ECG signal, nor both, will effectively distinguish the His signal from the background noise on the body surface.

The most effective way to date of accurately measuring His bundle activity has been the method suggested by Scherlag et al. in 1969, which requires cardiac catheterization. B. J. Scherlag et al., "Catheter Technique for Recording His Bundle Activity in Man," *Circulation*, 39:13, 1969. In this method, an electrode catheter is inserted percutaneously into the right femoral vein and advanced fluoroscopically into the right atrium so that at least two of the electrode poles straddle the tricuspid valve. The His signal appears as a high frequency spike between the P-wave and the QRS complex on the ECG tracing. While this method eliminates the problems with surface noise, it is an invasive technique which carries with it many significant risks associated with cardiac catheterization. Surface measurement of heart activity, i.e., a totally noninvasive technique, is much preferred.

Signal averaging techniques have been employed in connection with the surface measurement of His signals. See, for example, E. J. Berbari et al., "Noninvasive Technique for Detection of Electrical Activity During the P-R Segment," *Circulation*, 48:1005, 1973; N. C. Flowers et al., "Surface Recording of Electrical Activity from the Region of the Bundle of His," *American Journal of Cardiology*, 33:384, 1974; Y. Hishimoto and T. Sawayama, "Non-Invasive Recording of His Bundle Potential in Man," *British Heart Journal*, 37:635, 1975; R. Vincent et al., "Noninvasive Recording of Electrical Activity in the PR Segment in Man," *British Heart Journal*, 40:124, 1978; H. Takeda et al., "Noninvasive Recording of His-Purkinje Activity in Patients with Complete Atrioventricular Block", *Circulation*, 60:421, 1979; N. El-Sherif et al., "Appraisal of a Low Noise Electrocardiogram," *Journal of the American College of Cardiology*, 1(2):456, 1983. Signal averaging has a number of disadvantages. In order to reduce the signal to noise ratio by a factor of 10, over 100 cycles must be averaged. Thus, the system is very slow to produce a desirable output. Also, since averaging assumes that the underlying signal remains constant, beat-to-beat changes in sequential cardiac cycles cannot be detected. If the reference point selected (usually the QRS complex) does not remain constant or is measured inaccurately, then the sharp spike of the His signal will become smoothed out and distorted in amplitude, duration and morphology.

The use of a shielded room to exclude electrically and magnetically generated background noise has been suggested. N. C. Flowers et al., "Surface Recording of His-Purkinje Activity on an Every-beat Basis Without Digital Averaging," *Circulation*, 63:498, 1981; S. N. Erne et al., "Beat to Beat Surface Recording and Averaging of His-Purkinje Activity in Man," *Journal of Electrocardiology*, 16(4):355, 1983. While these systems do yield beat-to-beat His signal variations, they are undesirable systems in that complex electronics and a costly, stationary shielded room must be used. Moreover, the use of shielded rooms and/or averaging of large numbers of cycles has, at best, yielded only equivocal results.

The use of a technique known as time-sequenced adaptive filtering for removing noise from a measured signal has been investigated. E. R. Ferrara, Jr., "The Time-Sequenced Adaptive Filter," Stanford University, Ph.D. Thesis (1978), whose work is based on Widrow's algorithm. See, for example, B. Widrow et al., "Stationary and Nonstationary Learning Characteristics of the LMS Adaptive Filter," *Proceedings of the IEEE*, 64:1151, 1976. Unlike a fixed frequency filter, an adaptive filter adjusts its parameters during operation to optimize its performance. The adjustable parameters of an adaptive filter are called weights; they are continually updated by an iterative procedure or algorithm which requires only minimal a priori knowledge about the signal. The algorithm adjusts the weights according to predetermined criteria so that the output is an optimized estimate of the signal. These criteria are embedded in the algorithm that updates the weights. In essence, the adaptive filter learns the statistics of the signal initially and then tracks them.

Two problems associated with the use of the Ferrara algorithm in detecting surface His signals have been investigated. M. T. Juran, "Surface Recordings of His-Purkinje Activity Using Adaptive Filtering," Carnegie-Mellon University, Masters Thesis (1984). These problems concern the effects of correlated noise in the input signals to the adaptive filter and the means to automatically compute the coefficient controlling the rate of learning of the filter. In addition, the Ferrara algorithm cannot accurately detect large beat-to-beat variations in the location of the His signal.

Therefore, it is an object of the present invention to provide an improved method and apparatus for surface detection of His signals which utilizes the concepts of time-sequenced adaptive filtering. The present invention will preserve the amplitude and high frequency characteristics of the sharp spike His signal in a real time data processing apparatus. The device will filter out the background noise and locate the His signal in a very short time, as short as 4 or 5 beats, and will accurately record beat-to-beat changes.

It is a further object to accomplish all of these requirements in a system which is portable, safe and easy to use, does not require complex electronics or a specially shielded room, and can be implemented on a programmed microcomputer.

SUMMARY OF THE INVENTION

Accordingly, we have invented a method and apparatus of detecting low level, surface bioelectric signals, such as His signals at the surface of the thorax of a patient, in a noninvasive manner. The detected bioelectric signals are enhanced by filtering out the interfering noise through a particular adaptive filtering technique.

In the detection of His signals, surface ECG signals are acquired at a plurality of external locations on the chest of a patient and the acquired signals are digitized by continuous sampling at a rate greater than the Nyquist rate. The now digitized signals are stored for processing. One of the ECG signals is selected to be a reference channel with the remaining signals referred to as the input channels. A feedback coefficient $u_j$ is calculated for each of a plurality of sample points $j$ in a cycle of the ECG signals. Thereafter, at least a portion of each cycle of each of the input channels is adaptively filtered using the reference channel as a base. The adaptive filtering includes conducting a first pre-updating of a weight matrix associated with sample point $j$ for each input channel with reference to an input channel sample immediately prior to sample point $j$. Then, a second pre-updating of the weight matrix associated with sample point $j$ is conducted for each input channel with reference to an input channel sample immediately subsequent to sample point $j$. Then, an output signal is calculated at sample point $j$ by multiplying each of the weight matrices at sample point $j$ by the associated input channel at the sample point $j$ and surrounding points as determined by the length of the weight matrix and totalling the products of the multiplication process. Thereafter, a final updating of each weight matrix associated with sample point $j$ is conducted with reference to the calculated output, the feedback coefficient $u_j$ and the reference channel signal and input channel signals at sample point $j$. The weight matrices calculated in this final updating are stored for use in a subsequent cycle.

The adaptive filtering steps are carried out for each sample point $j$ in a particular cycle and then the entire process is repeated sequentially for each cycle of the acquired ECG signals. The output signal is displayed to give a reading indicative of a patient's electrocardiagraphic potential.

The calculated output signal is preferably stored in a storage register for the reference channel prior to being displayed. It is preferred that only a portion of each cycle be adaptively filtered, such as a 400 millisecond period prior to the onset of the QRS complex or following the onset of the P-wave. The reference channel is preferably selected as the surface ECG signal which has the least noise.

In one embodiment of the invention, the ECG signals measured at the surface are filtered by a bandpass filter having a lower cut-off of about 40 Hertz and an upper cut-off of about 400 Hertz, with the digital sampling rate per channel being 1000 samples per second. At a minimum, surface ECG signals are acquired at two external locations on a patient and the weight matrix associated with each sample point of interest has five weights. The feedback coefficient, which is asked in updating of the weight matrix, is preferably calculated by comparing the variance of the noise with the square of the magnitude of the input channel signal at a particular sample point. If the magnitude squared is greater than the variance of the noise, then the feedback coefficient is calculated using the inverse of the magnitude squared, otherwise the feedback coefficient is calculated using the inverse of the variance of the noise. Preferably, the surface ECG signals are acquired at locations such that the detected ECG signals have a similar morphology.

DETAILED DESCRIPTION OF THE PREFERRED EMBODIMENTS

Figure 1:
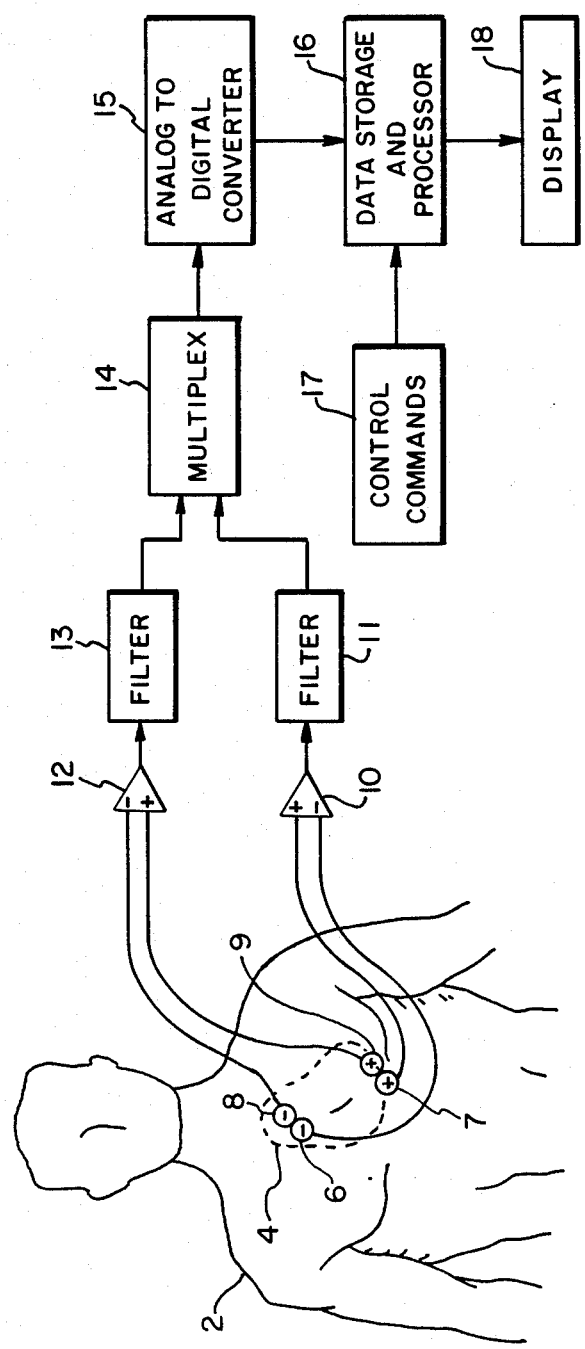
FIG. 1 is a block diagram showing the major components of the His signal detection apparatus of the present invention.

FIG. 1 is a block diagram of one embodiment of a His signal detection system in accordance with the present invention. A patient 2 has two pairs of surface electrodes positioned on the surface of the chest near the patient's heart 4. For purposes of clarity only two electrode pairs have been shown in FIG. 1. As will be explained hereinafter in more detail, any number of electrode pairs greater than one can be used in this invention. The surface electrodes can be the standard silver/silver chloride electrodes known in the art. One electrode of each pair is placed over the atria of the heart 4 and the other electrode of each pair is placed over the apex of the heart 4. As shown, electrode 6 of a first electrode pair and electrode 8 of a second electrode pair are placed over the atria of the heart 4, with electrode 8 preferably placed immediately above electrode 6. Electrode 7 of the first electrode pair and electrode 9 of the second electrode pair are placed over the apex of the heart 4, with electrode 9 preferably placed immediately above electrode 7. By such a placement of the electrodes, it is possible to measure at the surface two ECG signals which have a highly correlated underlying signal, i.e., the signals have a similar morphology representative of the ECG of the heart, and in which the noise is not highly correlated. By morphology, applicants are referring to the shape or form of the measured ECG waveforms. Since the muscle activity at the two different locations is a purely local function, the noise will be sufficiently different in the two electrode pairs. The signal measured by the first electrode pair 6,7 is fed to amplifier 10 and is thereafter filtered in bandpass filter 11. Similarly, the signal measured by the second electrode pair 8,9 is supplied to amplifier 12 and is thereafter filtered in bandpass filter 13. The amplifiers 10,12 have a gain of about 270,000 since the detected signals are of rather low magnitude. Filters 11 and 13 are preferably standard bandpass filters but, unlike standard surface ECG bandpass filters, filters 11 and 13 have a lower limit of about 40 Hertz and an upper limit of about 400 Hertz. It is important in this system to keep, particularly, the high frequency components of the measured signals since the His signal is of such short duration and has a significant high frequency content.

Thereafter, the analog signals from filters 11 and 13 are fed to multiplexer 14 where the data is sequenced. The signals are thereafter digitized in a standard analog-to-digital converter 15. While the use of a multiplexer 14 and a single analog-to-digital converter is preferred, it is possible to eliminate the multiplexer 14 and use a separate analog-to-digital converter for each filter. The measured signals are digitized by sampling the measured data at a sufficiently fast rate so that the underlying information is retained. The data should be sampled at a rate greater than the Nyquist rate for the signal. This rate is, at a minimum, two times the highest frequency component included in the signal. Since the filters 11 and 13 eliminate frequency components over about 400 Hertz, the Nyquist rate for this system is at least 800 Hertz and, accordingly, a 1,000 Hertz sampling rate has been selected as being adequate. Therefore, the measured data in each channel is sampled once every millisecond to digitize the analog data into a form suitable for processing by a programmed digital computer. The digitized data is supplied to a data storage and processor 16. The data is analyzed and adaptively filtered in accordance with instructions from the control commands 17 and the data, either the raw data or the adaptively filtered data, can be visualized on a display means 18.

Figure 2:
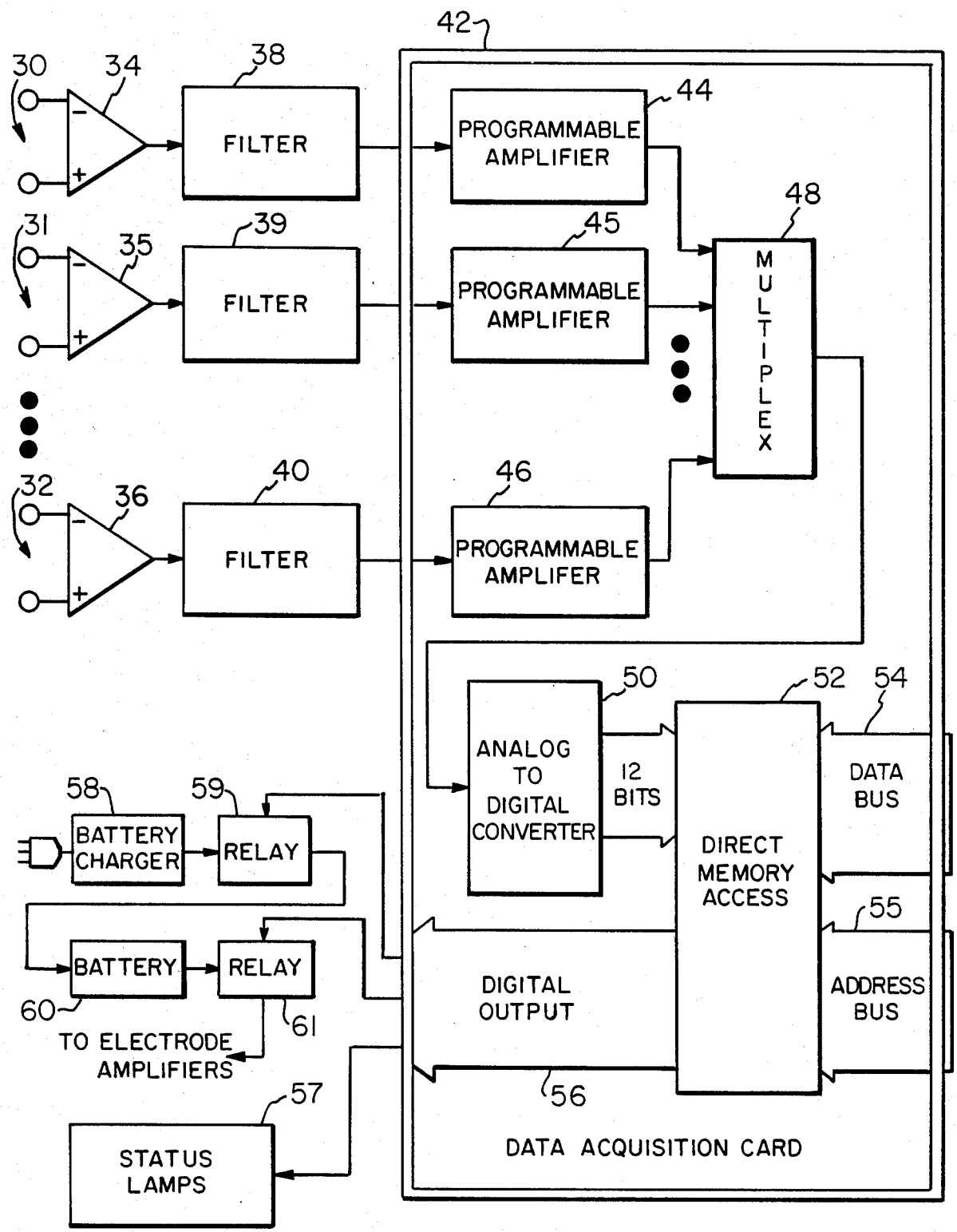
FIG. 2 is a block diagram of the data acquisition portion of the system shown in FIG. 1.

FIG. 2 shows, in block diagram format, a more detailed layout of the data acquisition portion of the system shown in FIG. 1. FIG. 2 shows the use of plurality of surface electrode pairs identified as first electrode pair 30, second electrode pair 31 and nth electrode pair 32. The signals measured by these surface electrode pairs are amplified in amplifiers 34, 35 and 36 and are thereafter bandpass filtered in filters 38, 39 and 40. As described above, filters 38, 39 and 40 are preferably bandpass filters which will screen out signal components below 40 Hertz and above 400 Hertz. Thereafter, the signals passing out of filters 38, 39 and 40 are supplied to a data acquisition card 42. In a commonly available data acquisition card, each input signal is supplied directly to a programmable amplifier. As shown in FIG. 2, the signal from filter 38 is supplied to programmable amplifier 44, the signal from filter 39 is supplied to programmable amplifier 45 and the signal from filter 40 is supplied to programmable amplifier 46. It is to be understood that there is an amplifier, filter, and programmable amplifier corresponding to each electrode pair used in the system.

The signals developed in the programmable amplifiers are supplied to multiplexer 48 where the data is sequenced and passed to analog-to-digital converter 50 where it is sampled at a 1000 Hertz rate and converted to digital form as described above in connection with FIG. 1. In a preferred embodiment of this invention, the data from the analog-to-digital converter 50 is represented in 12 bit format and is supplied to a direct memory access 52. The direct memory access 52 is a well known portion of the data acquisition card 42 and is used to store the incoming data, supply information between the direct memory access 52 and the central processor via data bus 54 and address bus 55, or pass an output signal along digital output bus 56. Certain information can be displayed from the central processor through direct memory access 52 and digital output bus 56 to one or more status lamps 57. Additional information can be used to control a battery charger 58, first safety relay 59, battery 60 and second safety relay 61. The output of the second control relay is supplied to the surface electrode amplifiers 34, 35 and 36. The use of relays 59 and 61 is a safety feature to ensure that the charger 58 is disconnected from the battery 60 when the system is in use and the system is inoperable when the batteries are being charged.

Figure 3:
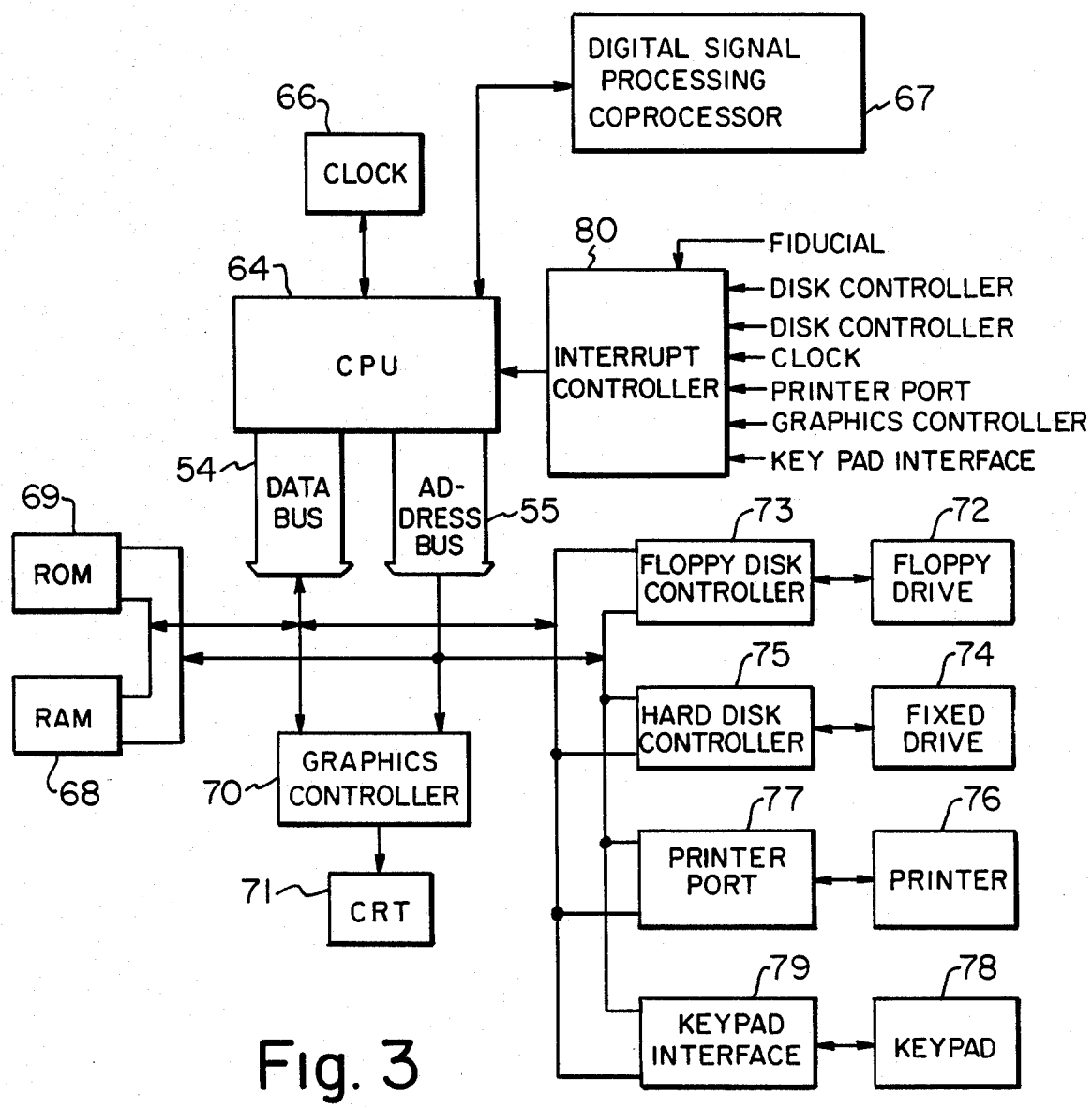
FIG. 3 is a block diagram of the remainder of the system shown in FIG. 1.

FIG. 3 shows a block diagram of the central processing portion of the system which is joined to the data acquisition portion of the system of FIG. 2 via data bus 54 and address bus 55. A central processing unit of CPU 64 receives and transmits data and addresses to the remainder of the system by way of data bus 54 and address bus 55. Clock 66 provides required timing information to CPU 64. A digital signal processing coprocessor 67 may also be used in conjunction with the CPU 64 to help speed up the activities of the CPU 64. The system also includes a random access memory 68 and a read-only memory 69, both connected to the data bus 54 and address bus 55. In addition, a graphics controller 70, connected to the data bus 54 and address bus 55, controls the system output which is shown on a CRT 71 or the like. Data can be supplied to and taken from the CPU 64 or the memories by means of a floppy disk drive 72 and floppy disk controller 73, a fixed drive 74 and associated hard disk controller 75, a printer 76 and associated printer port 77 and a keypad 78 and associated keypad interface 79. The floppy disk controller 73, hard disk controller 75, printer port 77 and keypad interface 79 are each connected to the data bus 54 and address bus 55.

Rather than have the CPU 64 periodically poll all of the various elements to determine whether any condition requiring immediate action has developed, it is preferable to directly control the CPU 64 by means of an interrupt controller 80. Interrupt controls that are useful in the present invention are a floppy disk controller interrupt, a hard disk controller interrupt, a clock interrupt, a printer port interrupt, a graphics controller interrupt, and a keypad interface interrupt. The fiducial interrupt shown in FIG. 3 is a special command which will be explained in more detail in connection with FIG. 4.

In analyzing the measured surface ECG information in a preferred embodiment of the present invention, it is necessary to determine a reference or trigger point in the underlying ECG signal. This triggering is controlled by detecting either the QRS complex or the P-wave of the measured ECG signal. Both of these signals are very distinct and are of much greater magnitude than the His signal and are therefore easy to detect and use as a trigger point for further filtering or processing of the measured data. In a preferred embodiment of the invention, the detection of either the QRS complex or the P-wave is carried out by the system software and no separate detection of these signals is necessary. In an alternative embodiment, it is possible to use a hardware trigger to detect either the QRS complex or the P-wave and to create what is referred to as a fiducial interrupt signal which would be supplied to the interrupt controller 80 of FIG. 3.

Figure 4:
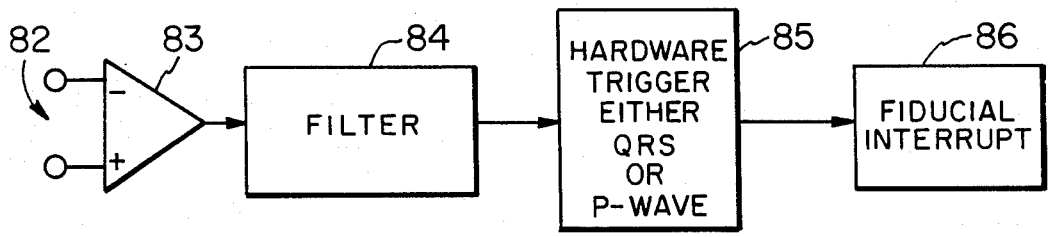
FIG. 4 is a block diagram of a hardware trigger.

FIG. 4 illustrates one arrangement utilizing a hardware trigger. This arrangement includes a surface electrode pair 82 whose output is supplied to amplifier 83, filter 84 and hardware trigger 85. The hardware trigger 85 generates a signal when either the QRS complex or the P-wave, as desired, is detected and creates a fiducial interrupt signal 86 supplied to the interrupt controller 80 in FIG. 3. The trigger looks for the highest amplitude signal and generates the output signal. Preferably, a surface electrode pair is used to generate a hardware QRS trigger since the QRS complex is very distinct and of strong magnitude at the surface when compared to the P-wave. If it is desired to use the P-wave as a trigger or fiducal interrupt, an esophageal or "pill" electrode can be used. A pill electrode, which is swallowed by the patient and is located near the patient's heart, is very efficient at detecting and generating a large P-wave signal. By the use of such a pill electrode, it is possible to create a hardware trigger which would identify the onset of the P-wave. A pill electrode is not considered to be an invasive technique and is only minimally more complicated than the use of a surface electrode.

Once the surface ECG data has been acquired and digitized in accordance with the hardware discussed in FIGS. 1-4 above, the remainder of the analysis of and computation on the acquired data will be conducted, preferably, in a programmed multipurpose digital computer. The control program can either be stored in hard disk and loaded into the random access memory 68 whenever the procedure is started or the program could be burned directly into the read only memory 69 and thereafter used by the central processor 64. Preferably, the data measured at the thorax of the patient is digitized and supplied directly to the random access memory 68 where it is thereafter used by the central processor 64.

Figure 5:
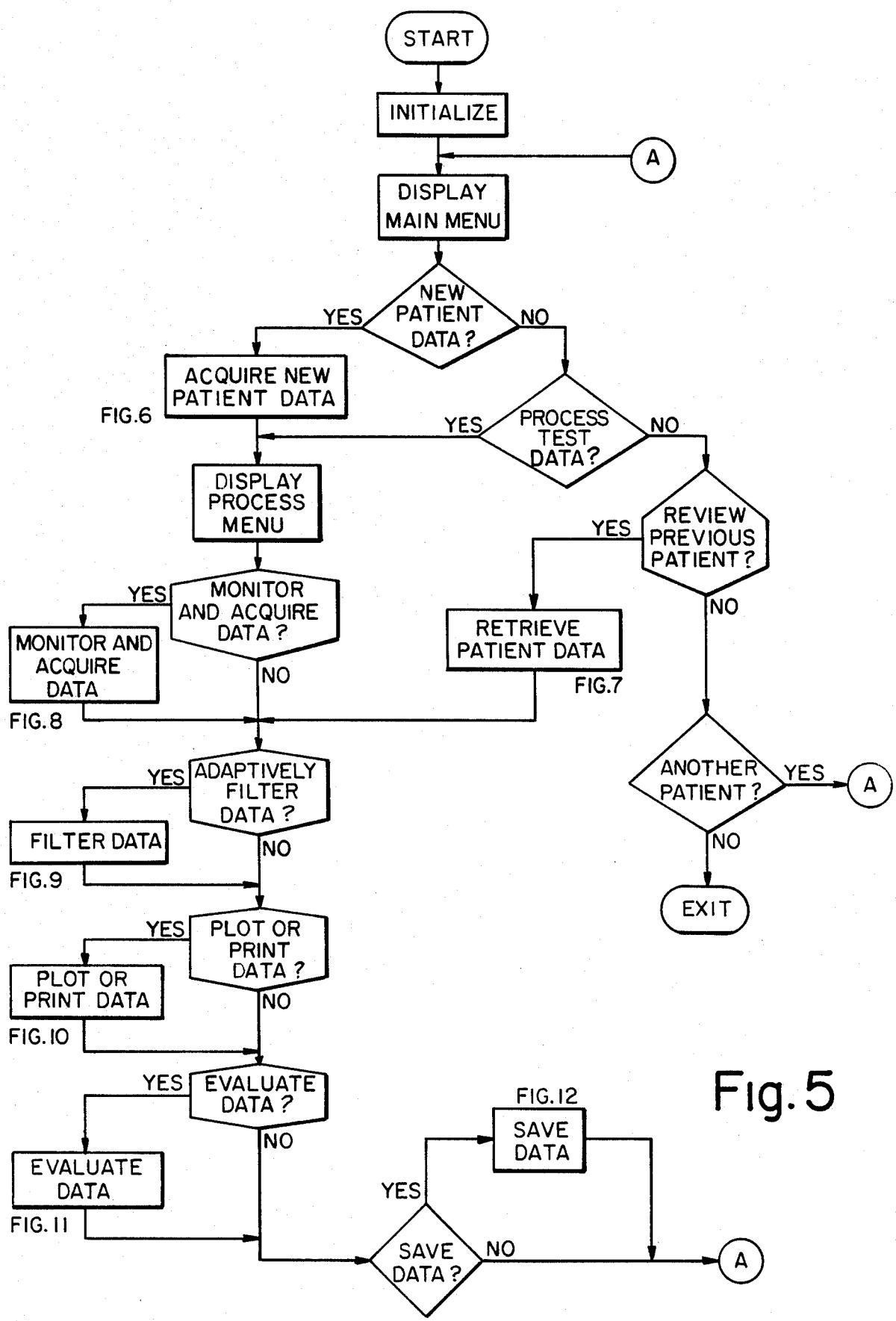
FIG. 5 is a flow chart of a main control program in accordance with the present invention.

FIG. 5 shows a flow chart of a main program suitable for use in the system of the present invention. Initially, the program is started and various registers and the like are initialized. Then, a main menu is displayed to the operator and a series of questions are presented. If a new patient is being monitored, then control passes to a subprogram where personal data about the new patient is acquired. If test data is going to be monitored, then the step of acquiring new patient personal data is bypassed. Thereafter, a process menu is displayed and another series of questions are presented in the main program loop. If data corresponding to surface ECG signals are to be monitored and acquired, control passes to an appropriate subprogram and then returned to the main program. Next, if the surface ECG data in the system is to be adaptively filtered, control passes to an appropriate subprogram and then returned to the main program. If the data is to be plotted or printed, control passes to an appropriate subprogram and then returned to the main program. If the data is to be evaluated, control passes to an appropriate subprogram and then returned to the main program. If data is to be saved, control passes to an appropriate subprogram and then returned to the main program. Thereafter, the main program loops back to the display of the main menu following the initialization process.

If the patient is not new and if test data is not to be processed, the program asks whether data previously collected from a patient is to be analyzed. If so, the patient's stored data is retrieved from a floppy disk with an appropriate subprogram and control passes to the main program loop immediately preceding the query on adaptive filtering. If a patient's previous data is not to be reviewed, the program queries whether another patient is to be monitored. If not, the program stops. If the answer is "yes," control passes to the beginning of the program and the above process steps are repeated.

Figure 6:
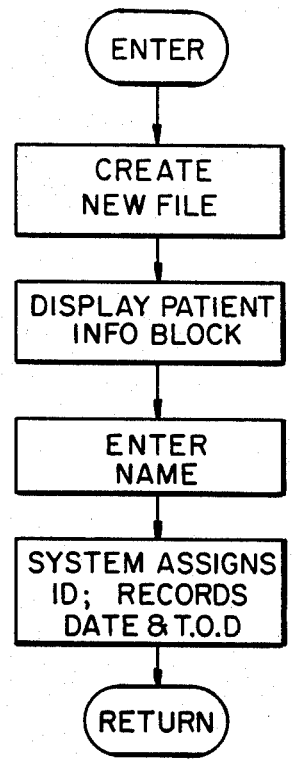
FIG. 6 is a flow chart of an acquire new patient data subprogram called by the main program in FIG. 5.

FIG. 6 is a flow chart of the acquire new patient data subprogram in FIG. 5. Initially, a new file is created, a patient information block is set up and the patient's name is entered. The subprogram then assigns an identification number, records the date and the time of day and returns control to the main program.

Figure 7:
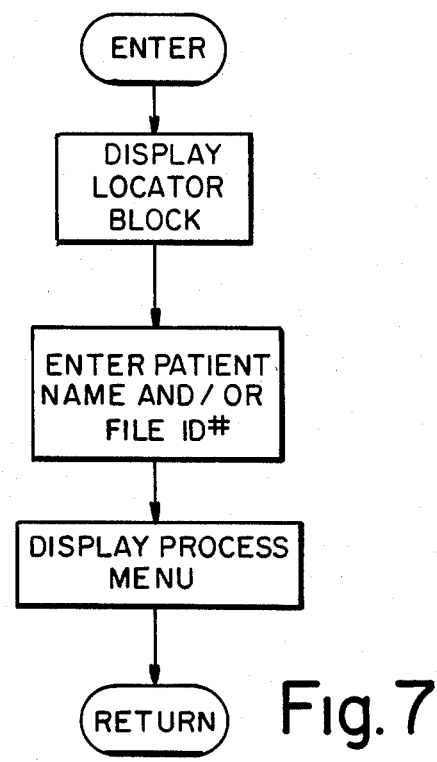
FIG. 7 is a flow chart of a retrieve patient data subprogram called by the main program in FIG. 5.

FIG. 7 is a flow chart of a retrieve patient data subprogram in FIG. 5. A locator block is displayed and the patient's name and/or file ID number are inserted into the locator block. The program then displays a process menu and the previously acquired patient data can be retrieved from the storage means on which it is stored. This data may be kept on floppy disk or hard disk or the like and is merely fed into the system from its storage source. Control is thereafter returned to the main program.

Figure 8:
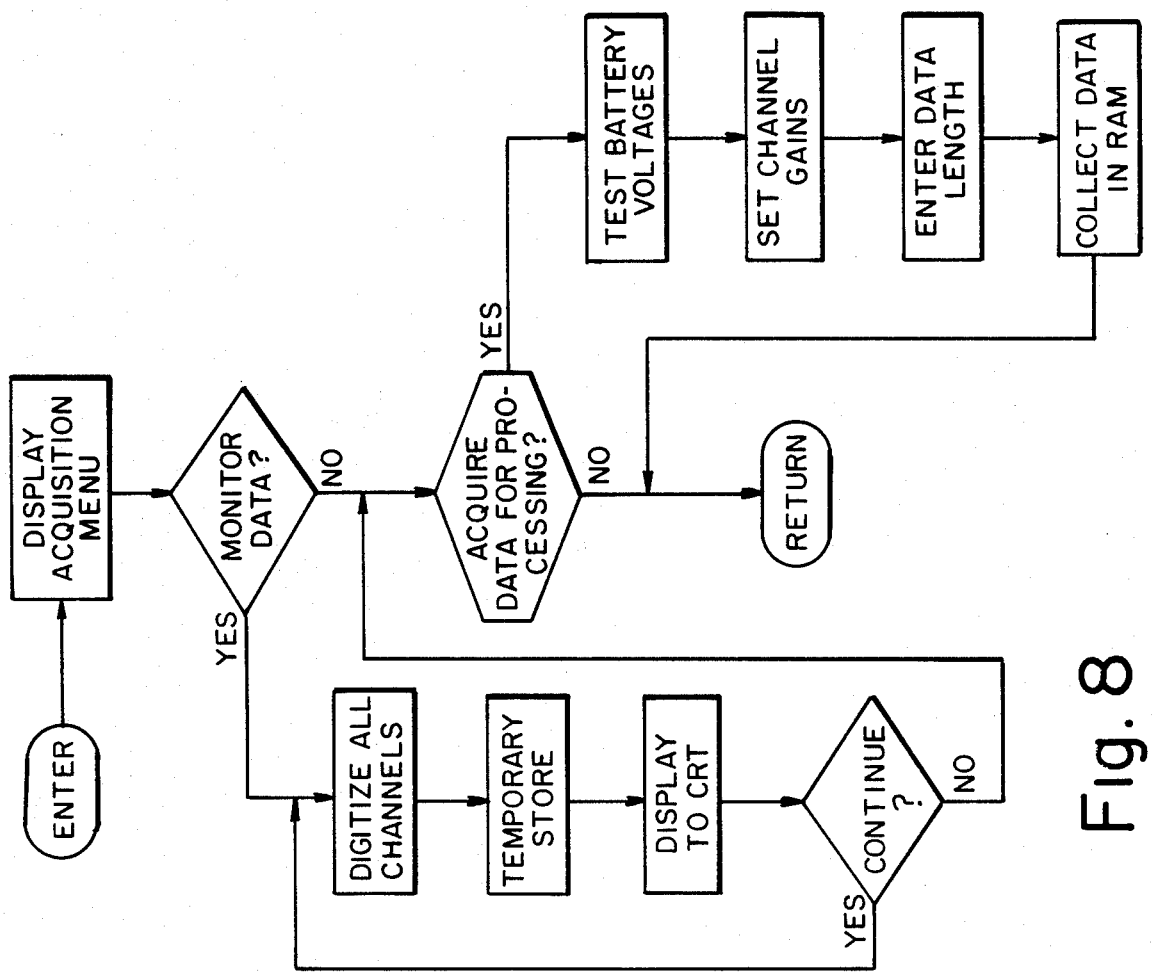
FIG. 8 is a flow chart of a monitor and acquire data subprogram called by the main program in FIG. 5.

A flow chart of a subprogram for monitoring and acquiring the data is shown in FIG. 8. Initially, an acqusition menu is displayed and the user decides whether to monitor the incoming data. If the incoming data is to be monitored, the data is digitized in all channels, temporarily stored and displayed to the CRT. This procedure can be continued repetitively if desired or, if not, control passes to the next query. The user is then asked whether the data should be acquired for processing. If not, control is returned to the main program. If the data is to be acquired, then the battery voltages are tested to see if they are sufficient, the channel gains are set to an appropriate level, the data length is entered and the data is collected into the random access memory. Thereafter, control is returned to the main program.

Figure 9:
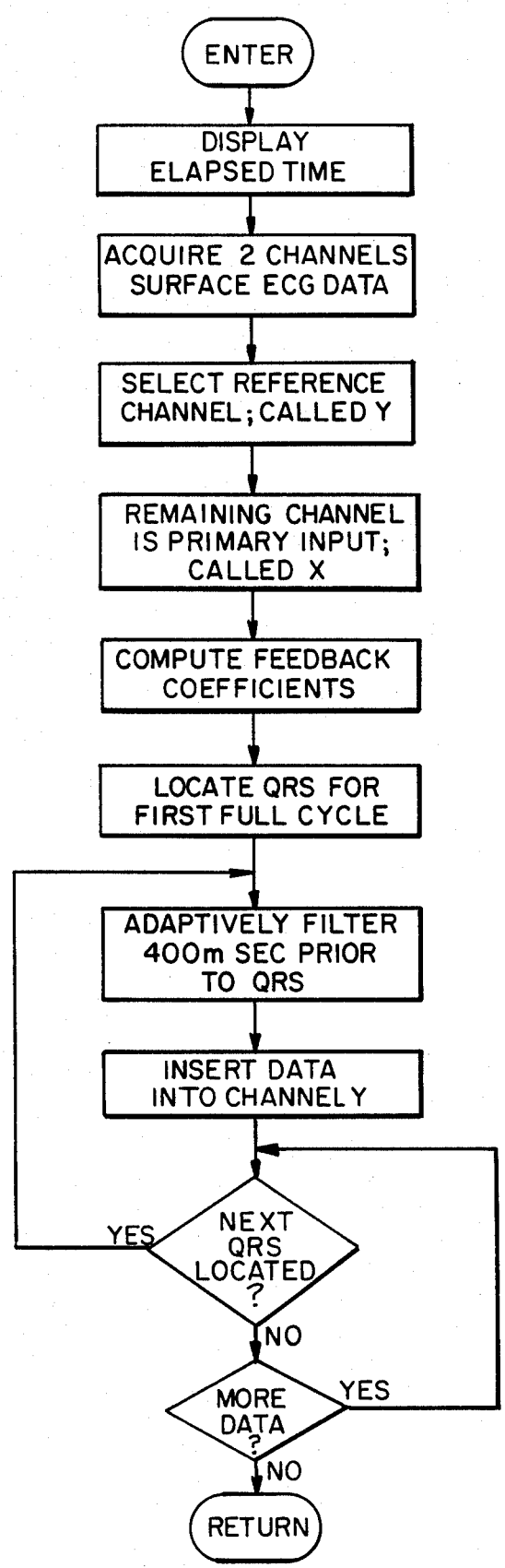
FIG. 9 is a flow chart of a filter data subprogram called by the main program in FIG. 5.

A subprogram suitable for adaptively filtering the data is shown in flow chart format in FIG. 9. Initially, the elapsed processing time is displayed and the channels of the surface ECG data are supplied to the subprogram. As shown in FIG. 9, only two channels are being measured, although it is to be understood that more than two channels can be utilized. Thereafter, one of the channels is selected as the reference channel and is called channel Y. This channel is selected on the basis of the channel which has the lesser noise. The remaining channel is referred to as the primary input and is identified as channel X. Then the feedback coefficients are computed for the data and used for the remaining processing in the adaptive filtering subprogram.

To carry out the adaptive filtering, it is only necessary to filter that portion of the measured data where the His signal will be located. Since the His signal is always located between the P-wave and QRS complex, it is possible to just filter a portion of the data prior to the QRS complex or following the P-wave. In the subprogram of FIG. 9, the QRS complex is selected for the reference point and a certain time period prior to the onset of the QRS complex, preferably 400 milliseconds, is adaptively filtered for a particular cycle. Thereafter, the time period in question is adaptively filtered utilizing the reference channel Y as a basis of measurement. After the primary channel has been adaptively filtered for the time period in question, this filtered data or modified data replaces the corresponding period in the Y channel, such as in a storage register, for later display or analysis or storage. The subprogram then searches for the next QRS complex; when it is located, the prior 400 millisecond period is filtered and the data stored. This process continues to the end of the data file. Control is then returned to the main program. The details of the adaptive filtering of the present invention are set forth in more detail hereinafter.

Figure 10:
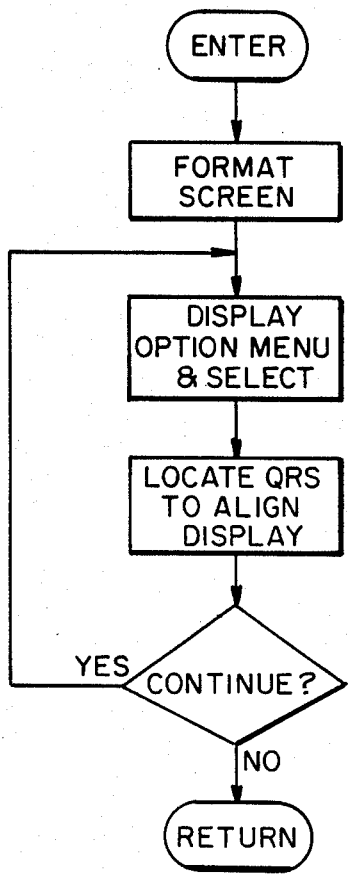
FIG. 10 is a flow chart of a plot or print data subprogram called by the main program in FIG. 5.

FIG. 10 is a flow chart of a plot or print data subprogram in which initially the screen display is formatted. Thereafter, an option menu is shown and the QRS complex is located to align and the display as desired. This can be repeated as many times as desired. Once the formatting is completed, the filter data can be either displayed on a CRT or printed or the like.

Figure 11:
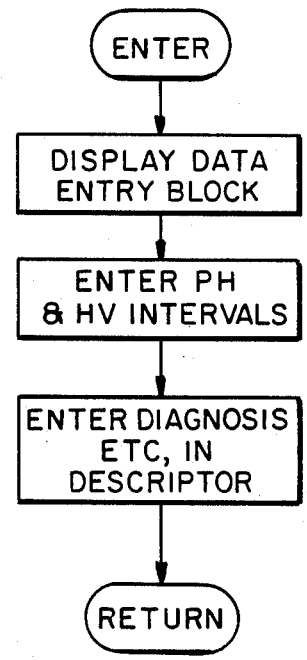
FIG. 11 is a flow chart of an evaluate data subprogram called by the main program in FIG. 5.
Figure 12:
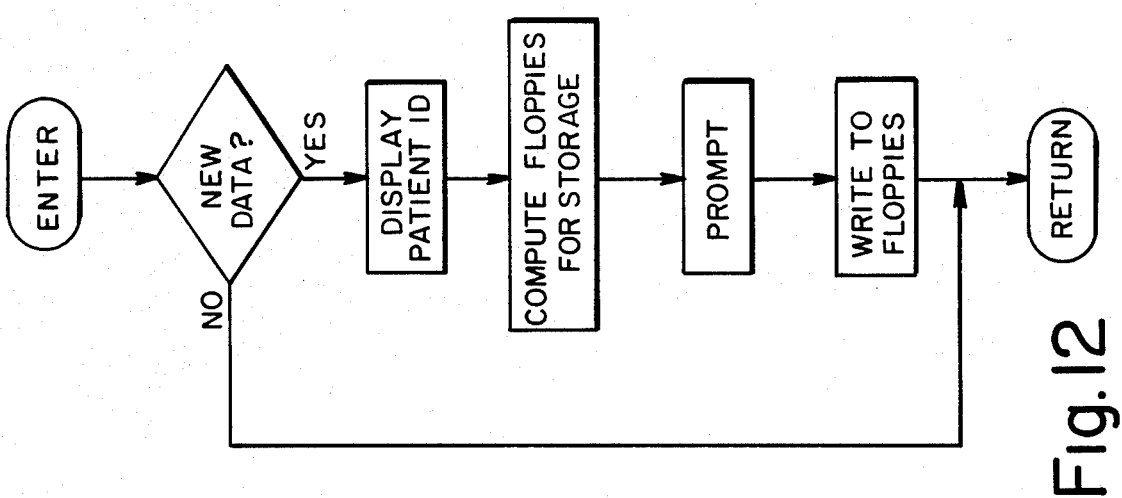
FIG. 12 is a flow chart of a save data subprogram called by the main program in FIG. 5.

It is often desirable to conduct immediate evaluations on the measured and/or filtered data and to enter such evaluation comments directly into the file record of the data. To that effect, the subprogram shown in block format in FIG. 11 is useful. Initially, a data entry block is displayed which enables the operator to enter certain identifying data. The P-H and H-V intervals can be entered, or various diagnostics or descriptors can be entered into the data entry block. Thereafter, control returns to the main program. After this step, the digitized ECG signals may be saved by using the save data subprogram shown in FIG. 12. The subprogram initially asks whether the data is new. If not, then control immediately returns to the main program since there is no need to store data which was previously stored. If the data is new, then the patient ID number is displayed, the subprogram computes a floppy disk number for storage, and upon prompting from the user stores this new data into the floppy disks or the like. Control is then returned to the main program.

The adaptive filtering carried out in the present application is based on a known technique for filtering noise from a repetitive or cyclic signal when a second signal having a highly correlated base signal, but uncorrelated noise, is available. The second signal is used as a reference signal. In general, the output for a specific point in time in a cycle is calculated by the following equation:

$$\text{output}_j = W_j \cdot X_j \quad (1)$$

where $W_j$ is a weight assigned to time point j and $X_j$ is the signal actually measured at time point j. The weight $W_j$ was calculated in a previous cycle and is merely used, unchanged, to generate the output in the current cycle. After the output is calculated, the weight $W_j$ is updated for the next cycle by using the following equations:

$$\text{error}_j = Y_j - \text{output}_j \quad (2)$$

$$\text{updated } W_j = W_j + 2 \cdot u \cdot \text{error}_j \cdot X_j \quad (3)$$

where u is an error feedback coefficient, a number greater than zero but less than infinity, $Y_j$ is the reference signal at time point j in the current cycle and $X_j$ is the signal measured at time point j in the current cycle.

In accordance with the present invention, several modifications are made to the above algorithm for adaptive filtering. Firstly, a matrix of weights, rather than one weight, is used for each filtered time point in a cycle. The weight matrix at sample point j is used and updated independently of the weight matrices at the remaining sample points of a cycle. In addition, the weight matrix is updated at least twice before the output is calculated and this pre-updating of the weight matrix is based on the measured signals at points of time surrounding the measured signal at the point of time being adaptively filtered. In a preferred embodiment, each point in time has weight matrix with five components and the pre-updating of the weight matrix is carried out using the digitized samples immediately preceding and immediately following the current sample point j.

This adaptive filtering technique can best be explained with the following equations, given with respect to a system having two channels of digitized data representing the measured ECG signals, where $X_j$ = input channel at a digitized sample point j in time
$Y_j$ = reference channel at sample point j
$u_j$ = feedback coefficient at sample point j
$W_{j,i}$ = weight matrix for sample point j.

The weight matrix $W_{j,i}$ is a one-by-N matrix vector where N is equal to twice the largest value for i plus one. In the following set of equations, the largest value of i is two, so the weight matrix or vector includes five elements at each sample point j. The first pre-updating of the weights is carried out with $X_{j-1}$, the input channel sample occurring just prior to sample point j, according to the following equations:

$$\text{error}'_j = Y_j - \sum_{i=-2}^{2} W_{j,i} \cdot X_{(j-1)+i} \quad (4)$$

For i from $-2$ to 2:

$$W_{j,i} = W_{j,i} + 2 \cdot u_j \cdot \text{error}'_j \cdot X_{(j-1)+i} \quad (5)$$

Using the five weights $W_{j,i}$ calculated above, a second pre-updating of the weight matrix is carried out using $X_{j+1}$, the input channel sample just after sample point j, as follows:

$$\text{error}''_j = Y_j - \sum_{i=-2}^{2} W_{j,i} \cdot X_{(j+1)+i} \quad (6)$$

For i from $-2$ to 2:

$$W_{j,i} = W_{j,i} + 2 \cdot u_j \cdot \text{error}''_j \cdot X_{(j+1)+i} \quad (7)$$

After the weight matrix has been pre-updated twice, the output at sample point j for a particular cycle is calculated as follows:

$$\text{output}_j = \sum_{i=-2}^{2} W_{j,i} \cdot X_{j+i} \quad (8)$$

The weight matrix is now updated, based on the calculated output, and this updated weight matrix is used for calculating the output at sample point j in the following cycle. The weight matrix is updated as follows:

$$\text{error}_j = Y_j - \text{output}_j \quad (9)$$

For i from −2 to 2:

$$W_{j,i} = W_{j,i} + 2 \cdot u_j \cdot \text{error}_j \cdot X_{(j+i)} \quad (10)$$

Thereafter, the computed output at sample point j is substituted for $Y_j$ in stored data, since the measured $Y_j$ is no longer needed, and the display of the output at sample point j is taken from the information now stored in $Y_j$.

Each time the weight matrix $W_{j,i}$ is multiplied by the input channel X at various sample points in time, a plurality of separate scalar multiplications are carried out. The resultant products are then summed together. For example, in the first pre-updating of the weight matrix in equation (4) above, the following products are summed together for sample point 50: $(W_{50,0} \cdot X_{49})$, $(W_{50,1} \cdot X_{50})$, $(W_{50,-1} \cdot X_{48})$, $(W_{50,2} \cdot X_{51})$ and $(W_{50,-2} \cdot X_{47})$. As another example, the following products are summed together for sample point 50 in the second pre-updating in equation (6) above: $(W_{50,0} \cdot X_{51})$, $(W_{50,1} \cdot X_{52})$, $(W_{50,-1} \cdot X_{50})$, $(W_{50,2} \cdot X_{53})$ and $(W_{50,-2} \cdot X_{49})$.

The above procedure is repeated for as many sample points as are desired in a cycle and the entire processing of a cycle is repeated for each cycle. In a preferred embodiment, each ECG signal is sampled at a rate of 1000 samples per second. Since the His signal is always located in the 400 msec interval before the onset of the QRS complex, a 400 msec sample period is selected. This results in 400 sample points and, accordingly, the above calculations are carried out, in each cycle, for j from 1 to 400.

The feedback coefficient $u_j$ is a number greater than zero and less than infinity and is selected to help stabilize the modification of the weights as quickly as possible without driving the system into an unstable or oscillatory mode. Preferably, the feedback coefficient is calculated for each sample point j in the portion of the cycle being analyzed. In general, the feedback coefficient is related to the inverse of the energy of the data. This cannot always be used because if the data had no energy, then the inverse would be infinity and an infinite feedback coefficient cannot be used. The feedback coefficient can be calculated as follows:

$$A_j = \frac{1}{\text{variance of noise}} \quad (11)$$

$$B_j = \frac{1}{X_j^2} \quad (12)$$

if $X_j^2 >$ variance of noise, (13)

then $u_j = B_j \cdot \gamma$ (14)

otherwise $u_j = A_j \cdot \gamma$ (15)

where $\gamma =$ (16)

$$\frac{\text{minimum error}}{\text{number of weights} \cdot \text{number of primary inputs.}}$$

The minimum error is a number selectable by the user and values between 0.002 and 0.005 have been found to be satisfactory.

The feedback coefficients are calculated prior to any adaptive filtering by looking at the first few cycles of the primary channel or channels and performing the above calculations. Thereafter, the feedback coefficients are used preferably without further update for a particular input signal. In general, the feedback coefficients should be large so as to speed-up the filtering process, but not too large so as to introduce instability into the system.

As discussed above, one of the channels of surface ECG signals is selected as the reference channel Y. This is an initial selection made prior to any adaptive filtering by calculating the variance of the noise in all channels, preferably in a quiet area without any underlying signal. The channel with the lowest noise variance is selected as the reference channel and the remaining channels are the input channels.

Since only a portion of the cycle contains the His signal, the entire cycle need not be adaptively filtered. It is preferred to pick a reference point and work backward or forward from that point to conduct the filtering. If the QRS complex from a surface electrode is used, then the highest magnitude signal is located and the stored input data 400 milliseconds prior to the QRS complex is filtered. If a pill electrode is used, the P-wave will have the highest magnitude. Therefore, the 400 milliseconds period following the high magnitude P-wave is adaptively filtered. Of course, periods of filtering greater or less than 400 milliseconds can be utilized as long as it covers the occurrence of the His signal.

A five weight matrix for each sample point j was selected because this gives a span of 5 milliseconds at a 1000 Hertz sample rate. The His signal is normally 10-15 milliseconds wide and a larger weight matrix will span beyond the width of the His signal and give no additional information. The use of a seven weight matrix was tested and found to add no improvements and a three weight matrix did not function as well. If a higher sample rate were used, then a larger weight matrix could be used to additional advantage.

While the weights in each weight matrix are based on the weights calculated in the previous cycle, the weights must be initialized to some value to start the system. In order to simplify matters, the initial weights are all preferably set at zero. The weights will quickly reach some number other than zero and it has been found that the algorithm will quickly reach a state where the weights accurately reflect the measured signals. Initial weights other than zero could also be used, if desired.

While equations (4)–(10) above have been given with respect to a two electrode pair system, i.e., a reference channel and an input channel, and with respect to a five weight matrix for each sample point j in time, a system including a plurality of electrode pairs and a larger weight matrix is another embodiment of the present invention, where $Xn_j$ = nth input channel at sample point j
$Y_j$ = reference channel at sample point j
$u_j$ = feedback coefficient at sample point j
$Wn_{j,i}$ = weight matrix for the nth input channel at sample point j
n = a whole number greater than zero
m = a whole number greater than one.

The weight matrix $Wn_{j,i}$ is a one-by-N matrix or vector where N is equal to twice m plus one.

The first pre-updating of each weight matrix associated with sample point j is carried out using a sample from each input channel just prior to sample point j, as follows:

$$\text{error}'_j = Y_j - \sum_{i=-m}^{m} W1_{j,i} \cdot X1_{(j-1)+i} - \ldots - \sum_{i=-m}^{m} Wn_{j,i} \cdot Xn_{(j-1)+i} \quad (17)$$

For i from −m to m:

$$W1_{j,i} = W1_{j,i} + 2 \cdot u_j \cdot \text{error}'_j \cdot X1_{(j-1)+i} \quad (18)$$

$$Wn_{j,i} = Wn_{j,i} + 2 \cdot u_j \cdot \text{error}'_j \cdot Xn_{(j-1)+i} \quad (19)$$

Using the weight matrices $W1_{j,i}$, $W2_{j,i}$, etc., calculated above, a second update of each weight matrix is carried out, using the input channels just after sample point j:

$$\text{error}''_j = Y_j - \sum_{i=-m}^{m} W1_{j,i} \cdot X1_{(j+1)+i} - \ldots - \sum_{i=-m}^{m} Wn_{j,i} \cdot Xn_{(j+1)+i} \quad (20)$$

For i from −m to m:

$$W1_{j,i} = W1_{j,i} + 2 \cdot u_j \cdot \text{error}''_j \cdot X1_{(j+1)+i} \quad (21)$$

$$Wn_{j,i} = Wn_{j,i} + 2 \cdot u_j \cdot \text{error}''_j \cdot Xn_{(j+1)+i} \quad (22)$$

After the weight matrices have been pre-updated twice, the output at sample point j is calculated as follows:

$$\text{output}_j = \sum_{i=-m}^{m} W1_{j,i} \cdot X1_{j+i} + \ldots + \sum_{i=-m}^{m} Wn_{j,i} \cdot Xn_{j+i}$$

The weight matrices are then updated for use in the following cycle as follows:

$$\text{error}_j = Y_j - \text{output}_j \quad (24)$$

For i from −m to m:

$$W1_{j,i} = W1_{j,i} + 2 \cdot u_j \cdot \text{error}_j \cdot X1_{j+i} \quad (25)$$

$$Wn_{j,i} = Wn_{j,i} + 2 \cdot u_j \cdot \text{error}_j \cdot Xn_{j+i} \quad (26)$$

In the above equations, the number n is one less than the number of surface electrode pairs since one electrode pair functions as the reference channel and the remaining electrode pairs are primary inputs. It will be recognized that the size of the weight matrix for each sample point of each primary channel is 2m+1. As an example, a five weight matrix would have an m=2. This is the embodiment discussed above in connection with equations (4)−−(10). The use of more than one primary channel will help to locate the His signal faster and will filter out the interfering noise more efficiently. However, the use of one primary channel is adequate.

Figure 13:
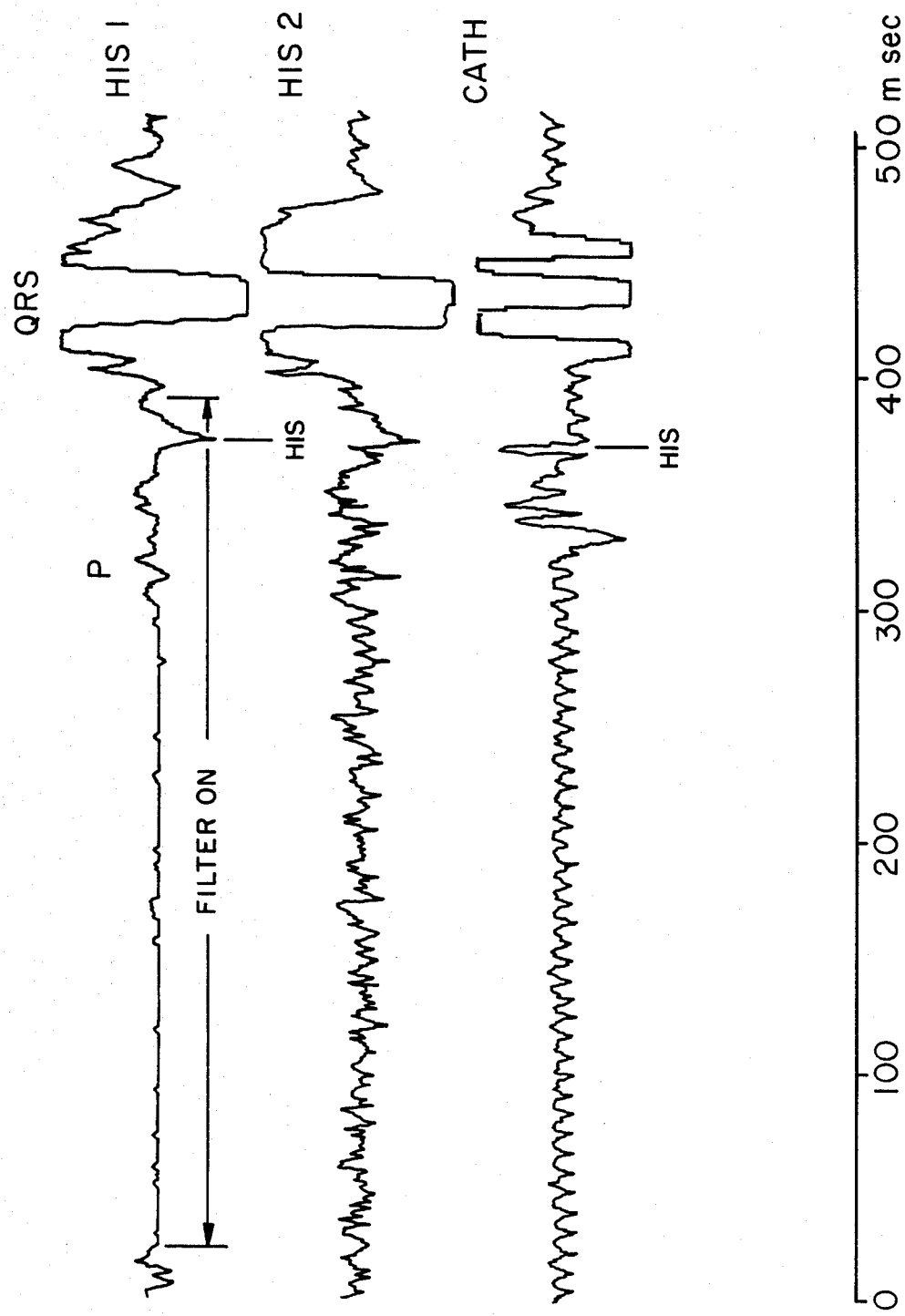
FIG. 13 is a graph showing several waveforms of a test conducted with the His signal detection apparatus of the present invention.
Figure 14:
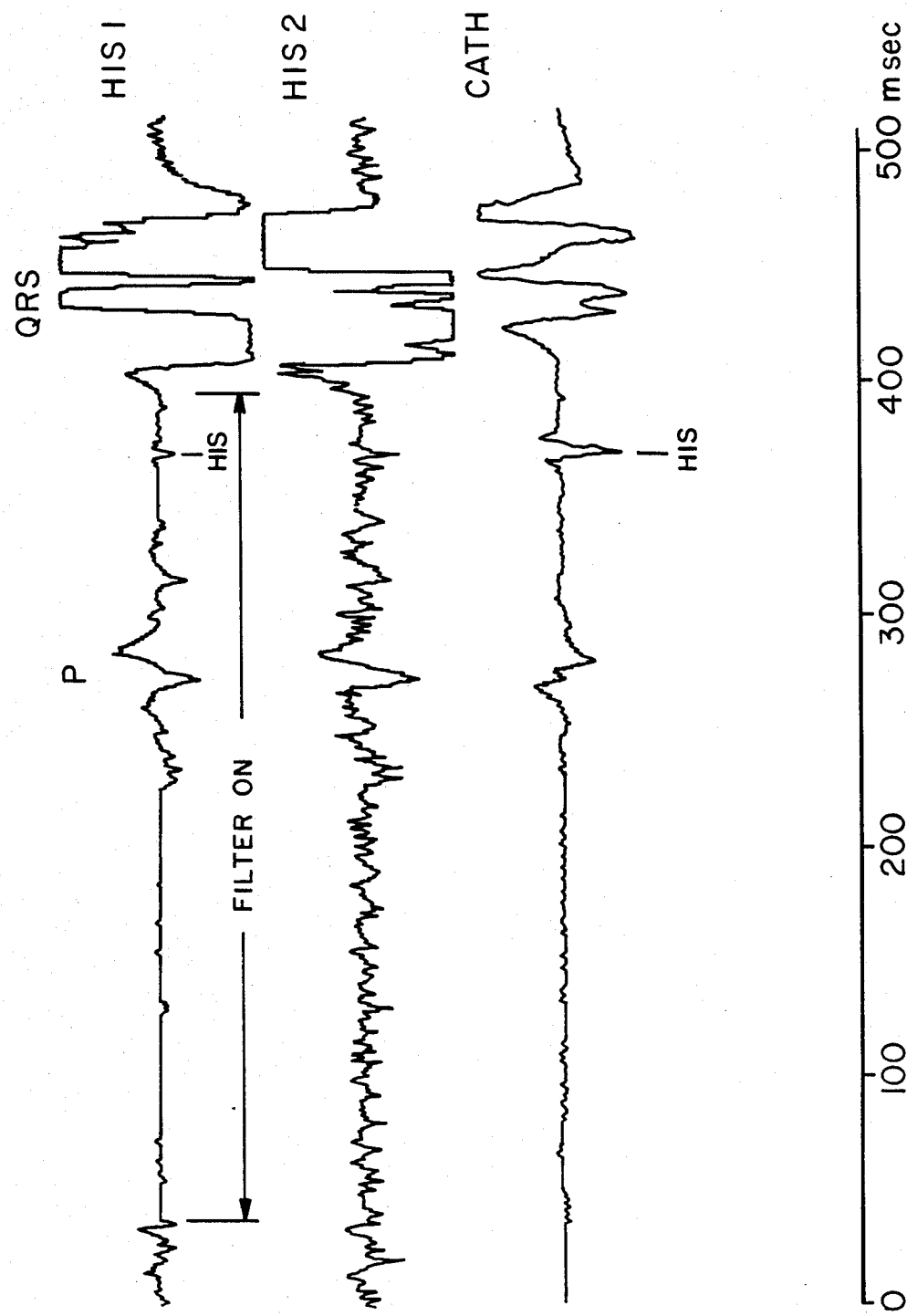
FIG. 14 is a graph similar to FIG. 13 showing several waveforms of another test.

An apparatus in accordance with the present invention using a five weight matrix for each sample point and only one primary input channel was built and tested on a patient in comparison with an intravenous catheter positioned in the patient's heart against the right atrial septum. The results of one test are set forth in FIG. 13 where the graph labeled "His 1" is the reference channel, with a portion of its data replaced by the adaptively filtered data, "His 2" is the unfiltered primary channel, and "Cath" is the output from the intravenous catheter. The filtered surface data (His 1) clearly locates the His signal from actual data (His 2) which does not distinguish the His signal from the background noise. The filtered data locates the His signal in precisely the same location as the intravenous catheter measurement. A similar test was conducted on another patient and the results are graphically illustrated on FIG. 14. Once again, the His signal cannot be distinguished from the background noise on the unfiltered channel (His 2) but the filtered data His signal compares favorably with the His signal measured by the intravenous catheter.

Having described above the presently preferred embodiments of the present invention, it is to be understood that it may otherwise be embodied within the scope of the appended claims.

We claim:

1. The method of detecting His signals at the surface of a patient comprising the steps of
   (a) acquiring a surface ECG signal at a plurality of external locations on the chest of the patient;
   (b) digitizing the acquired ECG signals by continuous sampling at a rate greater than the Nyquist rate;
   (c) storing said digitized ECG signals;
   (d) selecting one of said ECG signals to be a reference channel, with the remaining ECG signals referred to as input channels;
   (e) calculating a feedback coefficient $u_j$ for each of a plurality of sample points j in a cycle of the ECG signals;
   (f) there-after adaptively filtering at least a portion of each cycle of each of the input channels including the steps of
      (i) conducting a first pre-updating of a weight matrix associated with sample point j for each input channel with reference to an input channel signal to one side of sample point j,
      (ii) conducting a second pre-updating of the weight matrix associated with sample point j for each input channel with reference to an input channel signal to the other side of sample point j,
      (iii) calculating an output signal at sample point j by multiplying each weight matrix at sample point j by the associated input channel at sample point j and surrounding points as determined by the length of each weight matrix and totalling the products of said multiplication,
      (iv) conducting a final updating of each weight matrix associated with sample point j with reference to the output calculated in step iii, the feedback coefficient $u_j$ and the reference channel signal and input channel signals at sample point j, and storing said weight matrices for use in a subsequent cycle, (v) repeating steps i-iv sequentially for each sample point j in a particular cycle, and
(vi) repeating steps i-v sequentially for each cycle of the acquired ECG signals, and
(g) displaying the output signal to give a reading indicative of the patient's electrocardiographic potential.

2. The method of claim 1 wherein
(a) the first pre-updating of each weight matrix is conducted using the equations:

$$\text{error}'_j = Y_j - \sum_{i=-m}^{m} W1_{j,i} \cdot X1_{(j-1)+i} - \ldots -$$

$$\sum_{i=-m}^{m} Wn_{j,i} \cdot Xn_{(j-1)+i}$$

and for i from −m to m $$W1_{j,i} = W1_{j,i} + 2 \cdot u_j \cdot \text{error}'_j \cdot X1_{(j-1)+i}$$

.
.
.

$$Wn_{j,i} = Wn_{j,i} + 2 \cdot u_j \cdot \text{error}'_j \cdot Xn_{(j-1)+i}$$

where $Xn_j$ is the nth input channel at sample point j, n is a whole number equal to one less than the number of surface ECG signals acquired, $Y_j$ is the reference channel at sample point j, m is a whole number greater than one and $Wn_{j,i}$ is the weight matrix for the nth input channel at sample point j.

(b) the second updating of each weight matrix is conducted using the equations:

$$\text{error}''_j = Y_j - \sum_{i=-m}^{m} W1_{j,i} \cdot X1_{(j+1)+i} - \ldots -$$

$$\sum_{i=-m}^{m} Wn_{j,i} \cdot Xn_{(j+1)+i}$$

and for i from −m to m $$W1_{j,i} = W1_{j,i} + 2 \cdot u_j \cdot \text{error}''_j \cdot X1_{(j+1)+i}$$

.
.
.

$$Wn_{j,i} = Wn_{j,i} + 2 \cdot u_j \cdot \text{error}''_j \cdot Xn_{(j+1)+i}$$

(c) the output at sample point j is calculated using the following equations:

$$\text{output}_j = \sum_{i=-m}^{m} W1_{j,i} \cdot X1_{j+1} + \ldots + \sum_{i=-m}^{m} Wn_{j,i} \cdot Xn_{j+1}$$

(d) the final updating of each weight matrix associated with sample point j is conducted using the following equations:

$$\text{error}_j = Y_j - \text{output}_j$$

and for i from −m to m $$W1_{j,i} = W1_{j,i} + 2 \cdot u_j \cdot \text{error}_j \cdot X1_{j+i}$$

.
.
.

$$Wn_{j,i} = Wn_{j,i} + 2 \cdot u_j \cdot \text{error}_j \cdot Xn_{j+i}$$

3. The method of claim 2 wherein said calculated output signal is stored prior to display in a storage register for the reference channel.

4. The method of claim 2 wherein only a portion of each cycle prior to the onset of a QRS complex is adaptively filtered.

5. The method of claim 4 wherein said filtered portion of each cycle is about 400 milliseconds in duration.

6. The method of claim 2 wherein only a portion of each cycle following the occurrence of a P-wave is adaptively filtered.

7. The method of claim 6 wherein said filtered portion of each cycle is about 400 milliseconds in duration.

8. The method of claim 2 wherein said reference channel is selected as the surface ECG signal having the lowest noise variance.

9. The method of claim 2 wherein the surface ECG signals are filtered by a bandpass filter having a lower cut-off frequency of about 40 Hz and an upper cut-off frequency of about 400 Hz and the ECG signals are digitized by sampling at a rate of about one thousand samples per second per channel.

10. The method of claim 2 wherein a surface ECG signal is acquired at two external locations and m is 2, giving a single weight matrix of five elements associated with each sample point of a single input channel.

11. The method of claim 1 wherein the feedback coefficient $u_j$ is calculated by comparing the amount of the variance of the noise with the square of the magnitude of the input channel signals at sample point j and if said magnitude squared is greater than the variance of the noise, $u_j$ is calculated using the inverse of said magnitude squared, otherwise $u_j$ is calculated using the inverse of the variance of the noise.

12. The method of claim 1 wherein the surface ECG signals are acquired at locations such that the detected ECG signals have a similar morphology.

13. The method of detecting His signals at the surface of a patient comprising the steps of
(a) acquiring a surface ECG signal at a pair of external locations on the chest of a patient;
(b) digitizing the acquired ECG signals by continuous sampling at a rate greater than the Nyquist rate;
(c) storing said digitized ECG signals;
(d) selecting one of said ECG signals to be a reference channel, with the other ECG signal identified as an input channel;
(e) calculating a feedback coefficient $u_j$ for each of a plurality of sample points j in a cycle of the ECG signals;
(f) there-after adaptively filtering at least a portion of each cycle of said input channel including the steps of
(i) conducting a first pre-updating of a weight matrix associated with sample point j with reference to the input channel signal immediately prior to sample point j using the following equations;

$$\text{error}'_j = Y_j - \sum_{i=-2}^{2} W_{j,i} \cdot X_{(j-1)+i}$$

and for i from −2 to 2

$$W_{j,i} = W_{j,i} + 2 \cdot u_j \cdot \text{error}'_j \cdot X_{(j-1)+i}$$

where $X_j$ is the input channel at a sample point j, $Y_j$ is the reference channel at sample point j, and $W_{j,i}$ is the weight matrix for sample point j, (ii) conducting a second pre-updating of the weight matrix associated with sample point j with reference to the input channel signal immediately subsequent to sample point j using the following equations:

$$\text{error}''_j = Y_j - \sum_{i=-2}^{2} W_{j,i} \cdot X_{(j+1)+i}$$

and for i from −2 to 2

$$W_{j,i} = W_{j,i} + 2 \cdot u_j \cdot \text{error}''_j \cdot X_{(j+1)+i}$$

(iii) calculating an output signal at sample point j using the equation:

$$\text{output}_j = \sum_{i=-2}^{2} W_{j,i} \cdot X_{j+i}$$

(iv) conducting a final updating of the weight matrix associated with sample point j using the following equations:

$$\text{error}_j = Y_j - \text{output}_j$$

and for i from −2 to 2:

$$W_{j,i} = W_{j,i} + 2 \cdot u_j \cdot \text{error}_j \cdot X_{(j+i)}$$

(v) repeating steps i–iv sequentially for each sample point j in a particular cycle, and (vi) repeating steps i–v sequentially for each cycle of the input channel, and (g) displaying the output signal to give a reading indicative of the patient's His potential with reference to the position of the P-wave and QRS complex.

14. An apparatus for detecting His signals at the surface of a patient comprising (a) means for acquiring a surface ECG signal at a plurality of external locations on the chest of the patient;

(b) means for digitizing the acquired ECG signals by continuous sampling at a rate greater than the Nyquist rate;

(c) means for storing said digitized ECG signals;

(d) means for selecting one of said ECG signals to be a reference channel, with the remaining ECG signals referred to as input channels;

(e) means for calculating a feedback coefficient $u_j$ for each of a plurality of sample points j in a cycle of the ECG signals;

(f) means for there-after adaptively filtering at least a portion of each cycle of each of the input channels including (i) means for conducting a first pre-updating of a weight matrix associated with sample point j for each input channel reference to an input channel signal to one side of sample point j.

(ii) means for conducting a second pre-updating of the weight matrix associated with sample point j for each input channel with reference to an input channel signal to the other side of sample point j, (iii) means for calculating an output signal at sample point j by multiplying each weight matrix at sample point j by the associated input channel at sample point j and surrounding points as determined by the length of each weight matrix and totalling the products of said multiplication, (iv) means for conducting a final updating of each weight matrix associated with sample point j with reference to the output calculated in step iii, the feedback coefficient $u_j$ and the reference channel signal and input channel signals at sample point j, and storing said weight matrices for use in a subsequent cycle, (v) means for sequentially conducting said first updating of the weight matrices, conducting said second updating of the weight matrices, calculating the output signal and conducting the final updating of the weight matrices for each sample point in a particular cycle, and (vi) means for repeating the adaptive filtering sequentially for each cycle of the acquired ECG signal, and (g) means for displaying the output signal to give a reading indicative of the patient's electrocardiographic potential.

15. The apparatus of claim 14 wherein (a) the means for conducting the first pre-updating of each weight matrix uses the equations:

$$\text{error}'_j = Y_j - \sum_{i=-m}^{m} W1_{j,i} \cdot X1_{(j-1)+i} - \ldots -$$

$$\sum_{i=-m}^{m} Wn_{j,i} \cdot Xn_{(j-1)+i}$$

and for i from −m to m:

$$W1_{j,i} = W1_{j,i} + 2 \cdot u_j \cdot \text{error}'_j \cdot X1_{(j-1)+i}$$

$$\vdots$$

$$Wn_{j,i} = Wn_{j,i} + 2 \cdot u_j \cdot \text{error}'_j \cdot Xn_{(j-1)+i}$$

where $Xn_j$ is the nth input channel at sample point j, n is a whole number equal to one less than the number of surface ECG signals acquired, $Y_j$ is the reference channel at sample point j, m is a whole number greater than one and $Wn_{j,i}$ is the weight matrix for the nth input channel at sample point j, (b) the means for conducting the second updating of each weight matrix uses the equation:

$$\text{error}''_j = Y_j - \sum_{i=-m}^{m} W1_{j,i} \cdot X1_{(j+1)+i} - \ldots -$$

$$\sum_{i=-m}^{m} Wn_{j,i} \cdot Xn_{(j+1)+i}$$

and for i from −m to m $$W1_{j,i} = W1_{j,i} + 2 \cdot u_j \cdot \text{error}''_j \cdot X1_{(j+1)+i}$$

$$\vdots$$

$$Wn_{j,i} = Wn_{j,i} + 2 \cdot u_j \cdot \text{error}''_j \cdot Xn_{(j+1)+i}$$

(c) the means for calculating the output at sample point j uses the following equation:

$$\text{output}_j = \sum_{i=-m}^{m} W1_{j,i} \cdot X1_{j+i} + \ldots + \sum_{i=-m}^{m} Wn_{j,i} \cdot Xn_{j+i}$$

(d) the means for conducting the final updating of each weight matrix associated with sample point j uses the following equations:

$$\text{error}_j = Y_j - \text{output}_j$$

and for i from −m to m $$W1_{j,i} = W1_{j,i} + 2 \cdot u_j \cdot \text{error}_j \cdot X1_{j+i}$$
$$\vdots$$
$$Wn_{j,i} = Wn_{j,i} + 2 \cdot u_j \cdot \text{error}_j \cdot Xn_{j+i}.$$

16. The apparatus of claim 15 further including a reference channel storage register to store said calculated output signal prior to display.

17. The apparatus of claim 15 wherein only a portion of each cycle prior to the onset of a QRS complex is adaptively filtered.

18. The apparatus of claim 17 wherein said filtered portion of each cycle is about 400 milliseconds in duration.

19. The apparatus of claim 15 wherein only a portion of each cycle following the occurrence of a P-wave is adaptively filtered.

20. The apparatus of claim 19 wherein said filtered portion of each cycle is about 400 milliseconds in duration.

21. The apparatus of claim 15 wherein said reference channel is selected as the surface ECG signal having the lowest noise variance.

22. The apparatus of claim 15 wherein the surface ECG signals are filtered by a bandpass filter having a lower cut-off frequency of about 40 Hz and an upper cut-off frequency of about 400 Hz and the ECG signals are digitized by sampling at a rate of about one thousand samples per second per channel.

23. The apparatus of claim 15 wherein a surface ECG signal is acquired at two external locations and m is 2, giving a single weight matrix of five elements associated with each sample point of a single input channel.

24. The apparatus of claim 14 wherein the feedback coefficient $u_j$ is calculated by comparing the amount of the variance of the noise with the square of the magnitude of the input channel signals at sample point j and if said magnitude squared is greater than the variance of the noise, $u_j$ is calculated using the inverse of said magnitude squared, otherwise $u_j$ is calculated using the inverse of the variance of the noise.

25. The method of claim 14 wherein the surface ECG signals are acquired at locations such that the detected ECG signals have a similar morphology.

26. An apparatus for detecting His signals at the surface of a patient comprising
(a) means for acquiring a surface ECG signal at a pair of external locations on the chest of a patient;
(b) means for digitizing the acquired ECG signals by continuous sampling at a rate greater than the Nyquist rate;
(c) means for storing said digitized ECG signals,
(d) means for selecting one of said ECG signals to be a reference channel, with the other ECG identified as an input channel,
(e) means for calculating a feedback coefficient $u_j$ for each of a plurality of sample points j in a cycle of the ECG signals,
(f) means for there-after adaptively filtering at least a portion of each cycle of said input channel including
  (i) means for conducting a first pre-updating of a weight matrix associated with sample point j with reference to the input channel signal immediately prior to sample point j using the following equations:

$$\text{error}'_j = Y_j - \sum_{i=-2}^{2} W_{j,i} \cdot X_{(j-1)+i}$$

and for i from −2 to 2

$$W_{j,i} = W_{j,i} + 2 \cdot u_j \cdot \text{error}'_j X_{(j-1)+i}$$

where $X_j$ is the input channel at sample point j, $Y_j$ is the reference channel at sample point j, and $W_{j,i}$ is the weight matrix for sample point j,
  (ii) means for conducting a second pre-updating of the weight matrix associated with sample point j with reference to the input channel signal immediately subsequent to sample point j using the following equations:

$$\text{error}''_j = Y_j - \sum_{i=-2}^{2} W_{j,i} \cdot X_{(j+1)+i}$$

and for i from −2 to 2

$$W_{j,i} = W_{j,i} + 2 \cdot u_j \cdot \text{error}''_j X_{(j+1)+i}$$

(iii) means for calculating an output signal at sample point j using the equation:

$$\text{output}_j = \sum_{i=-2}^{2} W_{j,i} \cdot X_{j+i}$$

(iv) means for conducting a final updating of the weight matrix associated with sample point j using the following equations:

$$\text{error}_j = Y_j - \text{output}_j$$

and for i from −2 to 2:

$$W_{j,i} = W_{j,i} + 2 \cdot u_j \cdot \text{error}_j X_{j+i}$$

(v) means for sequentially conducting said first updating of the weight matrix, conducting said second updating of the weight matrix, calculating the output signal and conducting the final updating of the weight matrix for each sample point in a particular cycle, and
  (vi) means for repeating the adaptive filtering sequentially for each cycle of the input channel, and
(g) means for displaying the output signal to give a reading indicative of the patient's His potential with reference to the position of the P-wave and the QRS complex.

27. The method of detecting low level bioelectric signals at the surface of a patient comprising the steps of
(a) acquiring a surface bioelectric signal at a plurality of locations on the surface of the patient;
(b) digitizing the acquired bioelectric signals by continuous sampling at a rate greater than the Nyquist rate;
(c) storing said digitized bioelectric signals;
(d) selecting one of said bioelectric signals to be a reference channel, with the remaining bioelectric signals referred to as input channels;
(e) calculating a feedback coefficient $u_j$ for each of a plurality of sample points j in a cycle of the bioelectric signals;
(f) there-after adaptively filtering at least a portion of each cycle of each of the input channels including the steps of
  (i) conducting a first pre-updating of a weight matrix associated with sample point j for each input channel with reference to an input channel signal to one side of sample point j,
  (ii) conducting a second pre-updating of the weight matrix associated with sample point j for each input channel with reference to an input channel signal to the other side of sample point j,
  (iii) calculating an output signal at sample point j by multiplying each weight matrix at sample point j by the associated input channel at sample point j and surrounding points as determined by the length of each weight matrix and totalling the products of said multiplication,
  (iv) conducting a final updating of each weight matrix associated with sample point j with reference to the output calculated in step iii, the feedback coefficient $u_j$ and the reference channel signal and input channel signals at sample point j, and storing said weight matrices for use in a subsequent cycle,
  (v) repeating steps i–iv sequentially for each sample point j in a particular cycle, and
  (vi) repeating steps i–v sequentially for each cycle of the acquired bioelectric signals, and
(g) displaying the output signal to give a reading indicative of the patient's bioelectric potential.

28. The method of claim 27 wherein
(a) the first pre-updating of each weight matrix is conducted using the equations:

$$\text{error}'_j = Y_j - \sum_{i=-m}^{m} W1_{j,i} \cdot X1_{(j-1)+i} - \ldots - \sum_{i=-m}^{m} Wn_{j,i} \cdot Xn_{(j-1)+i}$$

and for i from $-m$ to $m$ $$W1_{j,i} = W1_{j,i} + 2 \cdot u_j \cdot \text{error}'_j \cdot X1_{(j-1)+i}$$
$$\vdots$$
$$Wn_{j,i} = Wn_{j,i} + 2 \cdot u_j \cdot \text{error}'_j \cdot Xn_{(j-1)+i}$$

where $Xn_j$ is the nth input channel at sample point j, n is a whole number equal to one less than the number of surface bioelectric signals acquired, $Y_j$ is the reference channel at sample point j, m is a whole number greater than one and $Wn_{j,i}$ is the weight matrix for the nth input channel at sample point j, (b) the second updating of each weight matrix is conducted using the equations:

$$\text{error}''_j = Y_j - \sum_{i=-m}^{m} W1_{j,i} \cdot X1_{(j+1)+i} - \ldots - \sum_{i=-m}^{m} Wn_{j,i} \cdot Xn_{(j+1)+i}$$

and for i from $-m$ to $m$ $$W1_{j,i} = W1_{j,i} + 2 \cdot u_j \cdot \text{error}''_j \cdot X1_{(j+1)+i}$$
$$\vdots$$
$$Wn_{j,i} = Wn_{j,i} + 2 \cdot u_j \cdot \text{error}''_j \cdot Xn_{(j+1)+i}$$

(c) the output at sample point j is calculated using the following equations:

$$\text{output}_j = \sum_{i=-m}^{m} W1_{j,i} \cdot X1_{j+1} + \ldots + \sum_{i=-m}^{m} Wn_{j,i} \cdot Xn_{j+1}$$

(d) the final updating of each weight matrix associated with sample point j is conducted using the following equations:

$$\text{error}_j = Y_j - \text{output}_j$$

and for i from $-m$ to $m$ $$W1_{j,i} = W1_{j,i} + 2 \cdot u_j \cdot \text{error}_j \cdot X1_{j+i}$$
$$\vdots$$
$$Wn_{j,i} = Wn_{j,i} + 2 \cdot u_j \cdot \text{error}_j \cdot Xn_{j+i}.$$

29. The method of detecting low level bioelectric signals at the surface of a patient comprising the steps of
(a) acquiring a surface bioelectric signal at a pair of locations on the surface of a patient;
(b) digitizing the acquired bioelectric signals by continuous sampling at a rate greater than the Nyquist rate;
(c) storing said digitized bioelectric signals;
(d) selecting one of said bioelectric signals to be a reference channel, with the other bioelectric signal identified as an input channel;
(e) calculating a feedback coefficient $u_j$ for each of a plurality of sample points j in a cycle of the bioelectric signals;
(f) there-after adaptively filtering at least a portion of each cycle of said input channel including the steps of
  (i) conducting a first pre-updating of a weight matrix associated with sample point j with reference to the input channel signal immediately prior to sample point j using the following equations:

$$\text{error}'_j = Y_j - \sum_{i=-2}^{2} W_{j,i} \cdot X_{(j-1)+i}$$

and for i from $-2$ to $2$ $$W_{j,i} = W_{j,i} + 2 \cdot u_j \cdot \text{error}'_j \cdot X_{(j-1)+i}$$

where $X_j$ is the input channel at a sample point j, $Y_j$ is the reference channel at sample point j, and $W_{j,i}$ is the weight matrix for sample point j, (ii) conducting a second pre-updating of the weight matrix associated with sample point j with reference to the input channel signal immediately subsequent to sample point j using the following equations:

$$\text{error}''_j = Y_j - \sum_{i=-2}^{2} W_{j,i} \cdot X_{(j+1)+i}$$

and for i from $-2$ to $2$ $$W_{j,i} = W_{j,i} + 2 \cdot u_j \text{error}''_j X_{(j+1)+i}$$

(iii) calculating an output signal at sample point j using the equation:

$$\text{output}_j = \sum_{i=-2}^{2} W_{j,i} \cdot X_{j+i}$$

(iv) conducting a final updating of the weight matrix associated with sample point j using the following equations:

$$\text{error}_j = Y_j - \text{output}_j$$

and for i from $-2$ to 2:

$$W_{j,i} = W_{j,i} + 2 \cdot u_j \text{error}_j X_{(j+i)}$$

(v) repeating steps i–iv sequentially for each sample point j in a particular cycle, and (vi) repeating steps i–v sequentially for each cycle of the input channel, and (g) displaying the output signal to give a reading indicative of the patient's bioelectric potential.

* * * * *

UNITED STATES PATENT AND TRADEMARK OFFICE
CERTIFICATE OF CORRECTION

PATENT NO. : 4,751,931

DATED : June 21, 1988

INVENTOR(S) : Stanley A. Briller and Gerald G. Cano

Page 1 of 2

It is certified that error appears in the above-identified patent and that said Letters Patent is hereby corrected as shown below:

Column 2 Line 55 "a priori" should be <u>italicized</u>.

Column 4 Line 13 "asked" should read --used--.

Column 6 Line 42 "of" should read --or--.

Column 8 Line 47 "acqusition" should read --acquisition--.

Column 9 Line 23 after "storage" (second occurrence) insert --.--.

Column 9 Line 33 after "align" delete --and--.

Column 13 Line 48 before "outputj" insert --23)--.

Column 14 Line 1 "(4)--(10)" should read --(4)-(10)--.

Claim 2 c) Column 15 Line 55 "$X1_{j+1}$" should read --$X1_{j+i}$--.

Claim 2 c) Column 15 Line 55 "$Xn_{j+1}$" should read --$Xn_{j+i}$--.

UNITED STATES PATENT AND TRADEMARK OFFICE
CERTIFICATE OF CORRECTION

PATENT NO. : 4,751,931

DATED : June 21, 1988

INVENTOR(S) : Stanley A. Briller and Gerald G. Cano

It is certified that error appears in the above-identified patent and that said Letters Patent is hereby corrected as shown below:

Claim 15 c) Column 19 Line 5 "$X1_{j+1}$" should read --$X1_{j+i}$--.

Claim 15 c) Column 19 Line 5 "$Xn_{j+1}$" should read --$Xn_{j+i}$--.

Claim 26 f) ii) Column 20 Line 38 "error"$jX_{(j+1)+i}$" should read --error"$j \cdot X_{(j+1)+i}$--.

Claim 28 c) Column 22 Line 25 "$Xn_{j+1}$" should read --$Xn_{j+i}$--.

Signed and Sealed this

Twenty-fifth Day of April, 1989

Attest:

DONALD J. QUIGG

*Attesting Officer*   *Commissioner of Patents and Trademarks*